United States Patent [19]

Winans

[11] 4,250,263

[45] Feb. 10, 1981

[54] METHOD OF PURIFICATION OF THERMALLY STABLE ENZYMES

[75] Inventor: Vida Winans, Downers Grove, Ill.

[73] Assignee: UOP Inc., Des Plaines, Ill.

[21] Appl. No.: 93,568

[22] Filed: Nov. 13, 1979

[51] Int. Cl.$^3$ .............................................. C12N 9/92
[52] U.S. Cl. .................................. 435/234; 435/814; 435/827; 435/853; 435/886
[58] Field of Search ............... 435/233, 234, 814, 183, 435/185-232

[56] References Cited

U.S. PATENT DOCUMENTS 3,948,728  4/1976  Roeschlau et al. ................... 435/814

OTHER PUBLICATIONS

Yamanaka, "D-Xylose Isomerase" in Methods in Enzymology, vol. IX, pp. 588-593 (1966).

Primary Examiner—Lionel M. Shapiro
Attorney, Agent, or Firm—James R. Hoatson, Jr.; Raymond H. Nelson; William H. Page, II

[57] ABSTRACT

A composition comprising intracellular or extracellular glucose isomerase may be purified by a method comprising heat treatment at a temperature from about 40° C. to about 80° C. The resultant enzyme solution, when utilized to prepare an immobilized enzyme system, is operationally equivalent to glucose isomerase purified by the traditional physico-chemical methods.

6 Claims, No Drawings

METHOD OF PURIFICATION OF THERMALLY STABLE ENZYMES

BACKGROUND OF THE INVENTION

It is known that fructose is substantially sweeter than glucose. Because the latter is relatively inexpensive and readily available, it is desirable to have an efficient and economical means of converting glucose to fructose. The alkali isomerization of glucose yields fructose, but the production of undesirable side products and the necessity of removing caustic and other materials from a food ingredient make this route unattractive. A preferred method of isomerization utilizing enzymes has the advantages of specificity of reaction and lesser likelihood of producing undesirable side products which must be removed before the fructose-containing material can be used in foods. The enzymes which effect the conversion of glucose to fructose are called glucose isomerases and are formed from such bacteria belonging, inter alia, to the genus Arthrobacter and the genus Actinoplanes. These enzymes are water soluble, and if they are merely added to aqueous solutions of glucose, recovery of enzyme for reuse is difficult and expensive. Using the enzyme only once also affords a process which is relatively expensive. Consequently, many techniques have been developed for immobilizing the enzyme in such a way that substantial enzymatic activity in isomerizing glucose to fructose is displayed while the enzyme itself remains rigidly attached to some water-insoluble support, thereby permitting reuse of the enzyme over substantial periods of time and for substantial amounts of glucose containing solutions. One illustration of a method for immobilizing an enzyme is found in Levy and Fusee, U.S. Pat. No. 4,141,857, where a polyamine is absorbed on a metal oxide such as alumina, the resulting composite is treated with an excess of bifunctional reagent, such as glutaraldehyde, so as to crosslink the amine, thereby entrapping the resulting polymer in the pores of the metal oxide, and thereafter contacting the mass with an enzyme to form covalent bonds between the pendant aldehyde groups and amino groups on the enzyme. It is highly desirable that the material used in making immobilized enzyme contain the desired enzyme, here glucose isomerase, in as chemically pure a state as possible, both to assure maximum loading on the support, and to assure that the immobilized enzyme product will be homogeneous in the kind of enzyme bound to the support, thereby insuring maximum specificity in the conversion of glucose to fructose.

SUMMARY OF THE INVENTION

A principal object of this invention is to provide a method of purifying thermally stable enzymes. One embodiment comprises heat treatment of a composition containing glucose isomerase, removing solids formed during said heat treatment, and recovering the solution. A more specific embodiment comprises heat treatment of a cell-free solution containing glucose isomerase at a temperature from about 40° C. to about 80° C. for a time from about 5 minutes to about 2 hours, removing solids produced thereby, and recovering the solution. A still more specific embodiment comprises application of the process to glucose isomerase produced by the genera Actinoplanes and Streptomyces. Other objects and embodiments will be apparent from the description herein.

DESCRIPTION OF THE INVENTION

Purification of an enzyme which is to be immobilized on a support matrix and which is to be utilized thereafter in an immobilized enzyme system has several purposes. One purpose is to maximize efficiency of immobilization, which is to say that it is desirable to immobilize the maximum amount of enzyme which is presented to a support maxtrix. Such a goal may be achieved by selectively removing from the enzyme preparation those materials which interfere with the enzyme immobilization process, or which compete with enzyme for sites on the support matrix which are responsible for enzyme immobilization. Another purpose of purification is to eliminate the materials which may be immobilized along with the enzyme and whose presence would be deleterious in some way to the desired enzymatic conversion. Such deleterious action would include a decrease in enzymatic activity, promotion of undesirable concurrent conversions, and a decrease in useful lifetime of the enzyme system.

In this context, purification of an enzyme may be defined in two somewhat different ways. On the one hand, purification may be associated with a selective increase in the proportion of enzyme present relative to the total proteinaceous matter. This definition is akin to the more-or-less conventional chemical concept of purification and is the traditional definition of purification. In the case of enzymes, this concept of purification is measured by specific activity of the enzyme preparation, i.e., units of enzyme activity per mg. of proteinaceous matter. On the other hand, purification may be associated with achievement of a condition or status of an enzyme-containing preparation such that the support matrix is "blind" to the presence of components other than enzyme. This definition is akin to selective removal of only those components which may interfere with the intended use of the desired component. In the case of enzymes used in immobilized enzyme systems, this latter concept of purification is measured by operational indicia, e.g., efficiency in immobilizing enzyme offered to the support matrix, specific activity of the immobilized enzyme system, specificity of the desired enzymatic reaction, useful lifetime of the immobilized enzyme system, stability of the immobilized enzyme system, etc. It must be emphasized that in this latter concept of enzyme purification specific activity of the enzyme preparation is an inadequate index and even may be misleading. Unless stated otherwise, "purification" when used herein relates to this latter concept of enzyme purification, in contradistinction to the traditional concept of purification.

The prior art describes a process for purification of glucose isomerase as exemplified in U.S. Pat. No. 4,077,842. In this method a water-miscible organic solvent, such as i-propyl alcohol, is added to an aqueous solution of the enzyme, resulting in precipitation of enzyme-inactive matter. Solids are removed, and the solution is treated with a soluble magnesium salt, thereby causing precipitation of an enzyme-magnesium complex which is recovered by suitable means. This method exemplifies traditional purification techniques.

Methods of purification such as that described above are laborious, time-consuming, and relatively expensive. The necessity of resorting to such complicated traditional methods of purification under some circumstances is not denied. For example, such a method of purification may be desirable where the enzyme needs to be stored for long periods, especially in a dried state. However, a discovery of the present invention is that a much simpler, yet equally effective, expedient is available where a thermally stable enzyme is to be used in an immobilized enzyme system. In particular, this invention is based on the unexpected discovery that heat treatment of a crude glucose isomerase-containing composition causes precipitation of materials whose removal affords a solution of glucose isomerase, from which the enzyme can be efficiently immobilized by a support matrix with the resulting immobilized enzyme system being operationally equivalent to those prepared from enzyme purified by traditional methods, such as the one described in the prior art.

Glucose isomerase is an example of a thermally stable enzyme. Enzymes with glucose isomerase activity are produced by many microorganisms, including those of the genus Streptomyces, Lactobacillus, Curtobacterium, and Actinoplanes. Examples of particular species of glucose isomerase producers from the above genera include: A. missouriensis, A. philippenesis, A. armeniacus, L. pentosus, L. breves, C. citreum, C. luteum, C. helvolum, etc. The Streptomyces are particularly rich in glucose isomerase producers, and examples of such species include olivochromogenes, venezuelae, coelicolor, aureus, griseolus, and virginiae. By way of illustration only, A. missouriensis may be cultured on a medium containing a suitable carbon source and other appropriate nutrients for a time sufficient to give maximum, or near maximum, glucose isomerase activity. Whole cells containing the enzymes are collected by suitable means, such as filtration, washed, then freeze dried and resuspended in a buffer at a pH of about 6 to about 8. In a preferred embodiment the buffer is selected from the group consisting of imidazole, phosphate, and tris(hydroxymethylamino)methane, and any combination thereof. It is contemplated within the scope of this invention that other buffers may be used, but not necessarily with equivalent results. In addition, if so desired, the buffered solution may also contain divalent cobalt ions in the range from about $10^{-4}$ to about $10^{-2}$ molar, and magnesium ions in the range from about $10^{-3}$ to about $10^{-1}$ molar.

To release the enzyme from the cells the cell walls must be ruptured. Examples of suitable means include chemical rupture, as by digestion with a lysozyme enzyme preparation, or physical rupture, as by rending the walls with sound waves (sonication) or mechanical grinding. In one embodiment the enzyme may be released by sonication at a temperature between about 0° C. and about 15° C. The cell debris which is formed may be removed by any means known to those skilled in art, as for example, by centrifugation, to afford a solution containing glucose isomerase. A method wherein the cell debris is not removed prior to heat treatment is also contemplated to be within the scope of this invention, although the results are not necessarily equivalent.

This crude extract of glucose isomerase is then subjected to a heat treatment which performs the dual function of deactivating other enzymes and precipitating undesired material. Such treatment comprises maintaining the glucose isomerase preparation at temperature from about 40° C. to about 80° C. for an interval from about 5 minutes to about 120 minutes. In a preferred embodiment the enzyme preparation is heated from about 55° C. to about 65° C. for a period from about 10 to about 30 minutes and longer. The preparation then is cooled rapidly to a temperature from about 0° C. to about 20° C., and material which precipitates is removed by suitable means, centrifugation for example, and discarded. The resultant solution of enzyme may then be immobilized directly.

In another embodiment of this invention the steps of cell rupture and heat treatment may be reversed. Thus, a suspension of cells containing intracellular glucose isomerase may be maintained at a temperature from about 40° C. to about 80° C. for a time from about 5 to about 120 minutes, but preferably from about 55° C. to about 65° C. for a period from about 10 to about 30 minutes and longer. The suspension is cooled rapidly to a temperature from about 0° C. to about 20° C., the cell walls are ruptured by suitable means, as previously described, and the mixture of cell debris and coagulated organic material is removed by suitable means, as by centrifugation. The clear supernatant solution may then be immobilized directly.

If it is so desired, the resultant enzyme preparation may be concentrated as by ultrafiltration or the preparation also may be dialyzed against a suitable buffer. Alternatively, the enzyme preparation resulting from heat treatment may be utilized as the crude enzyme source in a more elaborate purification scheme, such as those based on solvent precipitation, or isoelectric point precipitation, or salt precipitation. It is to be emphasized, however, that immobilization of enzyme from the heat-treated preparation alone gives an immobilized enzyme system which is operationally equivalent to that obtained from the more highly purified preparations.

The following examples illustrate the process of this invention and it is to be understood that this invention is not limited thereto.

EXAMPLE 1

Actinoplanes missouriensis (NRRL-3342) was cultured aerobically at 29° C. in a fermentor using the following medium (per 10 liters):

| | |
|---|---|
| 200 g. | Casein Hydrolysate |
| 100 g. | Yeast Autolysate |
| 50 g. | NaCl |
| 5 g. | L-Cystine |
| 5 g. | $Na_2SO_3$ |
| 30 ml. | 1 M $M_gSO_4$ . $7H_2O$ |
| 500 ml. | 1 M Potassium phosphate buffer, pH 7.0 |
| 50g./500 ml. | Galactose, autoclaved separately |

Cells were harvested by filtration after an inoculum of 0.05 volume of fresh, mature cultures. The cell paste was washed once with 0.05 M phosphate buffer, pH 7.0, containing 9 g. NaCl per liter to give a yield of cells of about 60 g. (dry weight) per 10 liters having an enzyme activity of about 1200/units/gram dry cells.

Glucose isomerase catalyzes formation of an equilibrium mixture of glucose and fructose. The method of enzyme assay utilized in these examples is to measure the initial rate of glucose formation from fructose at 60° C. as opposed to the usual assay method which measures the initial rate of fructose formation from glucose. A 1.0 ml. portion of appropriately diluted enzyme or enzyme-containing cells was mixed with an assay solution which contained fructose, 2.5 M, tris(hydroxymethylamino)methane hydrochloride buffer, $2 \times 10^{-2}$ M, at pH 7.5, magnesium sulfate, $5 \times 10^{-3}$ M, and cobaltous chloride, $5 \times 10^{-4}$ M. After incubation at 60° C. for 30–60 minutes the reaction was terminated by addition of 1 ml of 0.1 N hydrochloric acid, and the glucose formed was measured with a glucose analyzer. One unit of glucose isomerase activity corresponds to formation of 1 micromole glucose per minute. Specific activity corresponds to micromoles of glucose formed per minute per milligram of protein used.

The freeze-dried cells were suspended in 50 mM immidazole buffer, pH 7.0, containing $10^{-2}$ M MgSO$_4$ and $10^{-3}$ M Co Cl$_2$, to a concentration of 5% (W/V) and subjected to sonic disintegration at about 8° C. for 12 minutes. The sonically disintegrated mixture was centrifuged at 12,000 rpm for 10 minutes and the cell debris discarded. The supernatant was heated at 60° C. for 20 minutes, then cooled quickly in an ice bath. Precipitated protein was removed by centrifugation (12,000 rpm for 10 min.) and discarded.

The specific activity, i.e., the units of enzyme activity per mg of protein present, was about 1.8 in the extract before heat treatment, and about 3.7 in the heat-treated preparation. Thus, heat treatment affords only a 2-fold increase in purity in the traditional sense.

A support matrix comprising gamma-alumina, 60–80 mesh, coated with polyethylenimine subsequently cross-linked with an excess of glutaraldehyde so as to furnish a plurality of pendant functional groups was used to immobilize the enzyme. The immobilization procedure included contacting, with agitation, the support matrix at a temperature from about 0° C. to about 20° C. with the enzyme solution at a pH from about 6 to about 8 for a time from about 6 to 30 hours. Excess solution was removed by decantation, the solid was washed with 2 M NaCl to remove adhering but mobile enzyme, and finally washed with water.

The immobilized enzyme system obtained thereby had an activity of 1150–1350 units per gram. The system was used as a fixed bed in the conversion of glucose to fructose, using 45% Cerelose as the feedstock at 60° C. and a pH of about 8 at a constant flow rate so as to afford initially about 42% conversion of glucose to fructose. The half-life of columns so prepared was 35–40 days.

For comparison, enzyme purified by more elaborate traditional means and which had a specific activity of about 16 units per mg. protein afforded immobilized enzyme systems whose activity was 1200–1400 units per gm. with half-lives of 35–40 days.

EXAMPLE 2

The heat treated enzyme preparation was concentrated by ultra-filtration, then dialyzed against a phosphate buffer at pH 7. The resulting enzyme was immobilized by the procedure described in Example 1 to afford an enzyme system whose activity was 1150 units per gm, and whose half-life under conditions of the aforementioned Example was 38 days.

EXAMPLE 3

The heat treated enzyme preparation was further purified by precipitation of glucose isomerase with acetic acid at pH 4. The resulting solid was redissolved in a phosphate buffer at pH 7 and dialyzed against this same buffer. Immobilization as described in the previous examples gave a system whose initial activity was 1350 units per g., with a half-life of 39 days under the conditions described in Example 1.

EXAMPLE 4

To show that the support matrix was loaded with enzyme to its maximum capacity the following experiments were run.

One gram of support was used to immobilize enzyme from heat treated solutions containing 1200, 1400, and 1700 units of glucose isomerase by the procedure given in Example 1. In each case the excess solution and rinses were analyzed for recovered enzyme, which amounted to 400, 600 and 900 units, respectively. Thus, 800 units of enzyme were loaded regardless of the amount afforded. In similar experiments where the enzyme was further treated as described in Example 2, 1000–2000 units of enzyme was offered to 1 gm. of support matrix. The final immobilized enzyme system in all cases had an activity of 1200–1300 units per gm.

The results of these experiments show the absence of material in the heat-treated enzyme preparation which would interfere with glucose isomerase immobilization.

What is claimed is:

1. A method of purifying glucose isomerase which consists of heating a glucose isomerase-containing solution at a temperature of from about 40° C. to about 80° C. for a time period of from about 5 to about 120 minutes to precipitate solid matter, separating the precipitated solid matter from the solution, and recovering the thus purified glucose isomerase solution.

2. The method of claim 1 wherein the cell walls of the glucose isomerase are ruptured after the heat treatment to form free enzymes and cell debris, and the cell debris is separated from the enzymes.

3. The method of claim 1 wherein said glucose isomerase is produced by microorganisms of the genera Actinoplanes and Streptomyces.

4. The method of claim 3 wherein said microorganisms of the genus Actinoplanes are species selected from the group consisting of missouriensis, philippinensis, and armeniacus.

5. The method of claim 3 wherein said microorganisms of the genus Streptomyces are species selected from the group consisting of olivochromogenes, venezuelae, coelicolor, aureus, griseolus, and virginiae.

6. The method of claim 1 wherein said purified solution is dialyzed.

* * * * *